(12) United States Patent
Xie et al.

(10) Patent No.: US 7,511,142 B2
(45) Date of Patent: Mar. 31, 2009

(54) MEDIATOR-MODIFIED REDOX BIOMOLECULES FOR USE IN ELECTROCHEMICAL DETERMINATION OF ANALYTE

(75) Inventors: Hong Xie, Singapore (SG); Zhiqiang Gao, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 447 days.

(21) Appl. No.: 10/900,599

(22) Filed: Jul. 28, 2004

(65) Prior Publication Data
US 2006/0025593 A1    Feb. 2, 2006

(51) Int. Cl.
*C07F 15/00* (2006.01)
*C12Q 1/26* (2006.01)

(52) U.S. Cl. .................. 546/2; 435/25; 435/6; 435/4; 436/84; 436/544; 436/547

(58) Field of Classification Search .............. 546/2; 435/4, 6, 25, 84, 544, 547
See application file for complete search history.

(56) References Cited

U.S. PATENT DOCUMENTS

| 6,352,824 | B1 | 3/2002 | Buck, Jr. et al. | |
|---|---|---|---|---|
| 6,676,816 | B2 | 1/2004 | Mao et al. | |
| 7,052,591 | B2 * | 5/2006 | Gao et al. | 204/490 |
| 2002/0090632 | A1 | 7/2002 | Buck, Jr. et al. | |

FOREIGN PATENT DOCUMENTS

WO    WO 96/25514    8/1996

OTHER PUBLICATIONS

Heller, A., *Acc. Chem Res*, 23:128-134 (1990).
Katz, E., *Anal. Chim. Acta*, 385:45-48 (1999).
Willner, I., et al., *Chem. Int. Ed.*, 39:1180-1218 (2000).
Xie, H., et al., *Nucleic Acids Research*, 32:e15 (2004).
Bartlett, P.N., et al., *Anal. Chem.*, 69:734-742 (1997).
Battaglini, F., et al., *Anal. Chem.*, 72:502-509 (2000).
Degani, Y., et al., *J. Phys. Chem.*, 91:1285-1289 (1987).
Badia, A., *J. Am. Chem. Soc.*, 115:7053-7060 (1993).
Battaglini, F., et al., *Bioconjugate. Chem.*, 5:430-435 (1994).
Xie, H., *Anal. Chem.*, 76(14):4023-29 (2004).
Habermüller, K., et al., *Electroanalysis*, 12(17):1383-1389 (2000).
http://chem.ch.huji.ac.il/~eugeniik/mediator4.htm, *The electrical contacting of mediator-modified enzymes*.

* cited by examiner

*Primary Examiner*—Charanjit S Aulakh
(74) *Attorney, Agent, or Firm*—Harness, Dickey & Pierce, P.L.C.; J. Timothy Keane; Kisuk Lee (57) ABSTRACT

Compositions and methods for electrochemical detection of an analyte comprising a transition metal compound

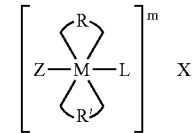

wherein M is a metallic element that can form a coordinate bond to nitrogen; R and R' are coordinated to M at their nitrogen atoms; L is a linking ligand; Z is chlorine or bromine; m can be from 1 to 6 and X is an anion, or combination of anions, that balances the charge m. Also provided are electrochemical tags and methods of detection.

75 Claims, 4 Drawing Sheets

MEDIATOR-MODIFIED REDOX BIOMOLECULES FOR USE IN ELECTROCHEMICAL DETERMINATION OF ANALYTE

FIELD OF THE INVENTION

This application relates generally to biosensors.

BACKGROUND OF THE INVENTION

Redox biomolecules undergo reversible reduction and oxidation and efficiently transfer electrons to a natural electron acceptor. They generally contain an active site prosthetic group or cofactor that mediates and participates in an oxidation and reduction pathway. Most commonly, the prosthetic group is based on dinucleotides such as flavin adenine dinucleotide (FAD) and nicotinamide adenine dinucleotide (NAD). The redox biomolecules oxidize and accept electrons from a substrate and then transfer the electrons by means of a reversible oxidation and reduction of the prosthetic group to an electron acceptor.

Biosensors can provide sensitive, rapid and low cost assays for detection of analytes in a sample. A biosensor essentially comprises a redox biomolecule that recognizes a target analyte and a transducer that converts the recognition event into a measurable signal. In one sense, the biosensor operates by "interrupting" the flow of electrons to the natural electron acceptor. The flow is detected as a current or voltage by an electrical circuit containing an electrode in proximity to the biomolecule. The transfer of electrons between the active site prosthetic group of the redox biomolecule and an electrode surface is thus an important factor in the efficient operation of biosensors.

It is generally observed that efficiency of electron transfer from redox biomolecules to the electrode surface of a biosensor is less than the highly efficient reduction of the natural electron acceptor. Several groups have investigated the modification of redox biomolecules by covalent attachment of a redox mediator, but found the electron transfer rate constants to be far lower than those between enzymes and their natural electron acceptor.

SUMMARY OF THE INVENTION

In accordance with the present invention, Applicants have successfully devised novel approaches in biosensors for detecting an analyte in a sample. The novel approaches are based on synthesis of novel oxidation reduction mediators that can lose or gain electrons under various experimental conditions. It is believed that such redox mediators act as electron relay groups that enable non-diffusion-mediated electron transfer from other oxidation reduction molecules such as, for example, oxidoreductases.

In various embodiments, the present invention provides transition metal compounds having a structure that corresponds to the formula I:

wherein M is a metallic element that can form a coordinate bond to nitrogen. R and R' can be nitrogen-containing organic moieties coordinated to M at their nitrogen atoms. L can be a linking ligand comprising an organic amine having from about 3 to about 20 non-hydrogen atoms, an aliphatic amino group and a nitrogenous moiety that provides a metal-to-nitrogen coordinate bond to M. Z can be a halogen atom and m can be +1, +2, +3, +4, +5, or +6. X is an anion, or combination of anions, that balances m.

In various other embodiments, the present invention also provides methods of preparing transition metal compounds having the above-described structure that corresponds to formula I. The method provides for contacting a precursor compound of the formula II:

wherein Z, M, R, R', X and m are as described above, with a linking ligand to form the transition metal compound of formula I via a ligand exchange reaction.

In further embodiments, the present invention provides an electrochemical tag comprising a redox biomolecule bonded to a transition metal compound of formula I wherein Z, L, M, R, R', X and m are as described above. In a preferred embodiment, M is osmium and L is 3-aminopropylimidazole. Preferably, the transition metal compound is covalently attached to the redox biomolecule, which preferably comprises glucose oxidase.

In various further embodiments, the present invention also provides methods for preparing the above-described electrochemical tags. The method comprises bonding a redox biomolecule to a transition metal compound of formula I wherein Z, L, M, R, R', X and m are as described above. In a preferred embodiment, Z is chlorine, L is 3-aminopropylimidazole and the transition metal compound is covalently attached to glucose oxidase by amide bond formation between glucose oxidase carboxylates and the aliphatic primary amino group present on L.

The present invention further provides methods for electrochemical detection of an analyte in a sample utilizing the above-described electrochemical tags. In various embodiments, an electrochemically active redox complex comprising the analyte and an electrochemical tag is formed at the electrode surface, wherein the electrochemical tag comprises a redox biomolecule bonded to a transition metal compound of formula I wherein Z, L, M, R, R', X and m are as described above. Without limiting the utility, function, or composition of the present invention, the shuttling of electrons between the electrochemical tag, which undergoes cycles of oxidation and reduction, to the electrode can be detected and is indicative of the presence or absence of the analyte in the sample. The analyte to be detected can be, for example, a nucleic acid or a protein. In a preferred embodiment, the analyte is a sequence corresponding to the p53 gene, which is a gene associated with a variety of cancers. In other embodiments, the analyte to be detected can also be the oxidation substrate for the redox biomolecule.

In still further embodiments, the present invention is also directed to kits comprising the above-described electrochemical tags, as well as, to biosensors that utilize such electrochemical tags for electrochemical detection of analytes.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF THE INVENTION

In accordance with the present invention, Applicants have devised novel biosensors and methods for detecting an analyte in a sample. The present invention is based on the synthesis of novel oxidation reduction mediators that can lose or gain electrons under various experimental conditions. Without being held to a particular theory, it is believed that such redox mediators act as electron relay groups that enable non-diffusion-mediated electron transfer from other oxidation reduction molecules such as, for example, oxidoreductases.

In various embodiments, the present invention provides transition metal compounds that can function as redox mediators and have structures that correspond to formula I described above wherein M is a metallic element that can form a coordinate bond to nitrogen. Suitable metallic elements for use as M can be, for example, osmium (Os), ruthenium (Ru), zinc (Zn), iron (Fe), rhodium (Rh), rhenium (Re), platinum (Pt), scandium (Sc), titanium (Ti), vanadium (V), cadmium (Cd), magnesium (Mg), copper (Cu), cobalt (Co), palladium (Pd), chromium (Cr), manganese (Mn), nickel (Ni), Molybdenum (Mo), tungsten (W), iridium (Ir) and mixtures thereof. In a preferred embodiment, the metallic element M is the transition metal osmium (Os).

R and R' can be the same or different and are coordinated to M at their nitrogen atoms. R, R', or both can be, for example, 2,2'-bipyridyl; 2,2'-bipyridyl substituted with one or more substituents selected from the group consisting of C1-C4 alkyl, phenyl and phenyl substituted with one or more C1-C4 alkyl groups; 1,10-phenanthrolinyl and 1,10-phenanthrolinyl substituted with one or more substituents selected from the group consisting of C1-C4 alkyl, phenyl and phenyl substituted with one or C1-C4 alkyl groups. Preferably, at least one of R and R' is 2,2'-bipyridyl.

L is a linking ligand. In various embodiments, L is an organic amine having from 3 to 20 non-hydrogen atoms, comprising an aliphatic amino group and further comprising a nitrogenous moiety that provides a metal-to-nitrogen coordinate bond to M. In a preferred embodiment, the nitrogenous moiety is a heterocyclic ring containing at least one nitrogen atom. Non-limiting examples include imidazole, benzimidazole, pyrroles, pyrazole, triazoles, benzotriazoles, pyridine, pyridazine, pyrazine, pyrimidine and triazines. One of the nitrogens of the heterocyclic ring forms a coordinate to the metal M. A preferred nitrogenous moiety is imidazole. When the nitrogenous moiety is a heterocyclic ring, the aliphatic amino group is preferably held on an alkyl group attached to the ring. The alkyl group may be straight chain or branched and contains generally from 1 to about 20 carbons, preferably from 2 to 12 and more preferably from 3 to 6 carbon atoms. A preferred linking ligand L is 3-aminopropylimidazole.

Z is a halogen atom. In a preferred embodiment Z is chlorine or bromine, more preferably chlorine. The superscript m can be +1, +2, +3, +4, +5, or +6, depending on the oxidation state of the metal M. In a preferred embodiment, for example when the metal M is osmium in the +4 oxidation state, Z is chlorine and m is +3. X is an anion, or combination of anions, that balances the formal charge m of the cation. For example, X can be, without limitation, chloride, bromide, iodide, fluoride, tetrafluoroborate, perchlorate, nitrate, sulfate, carbonate, or sulfite.

In other embodiments, at least one and preferably both, of the liganding groups R and R' is a 2,2'-bipyridyl or 1,10-phenanthrolinyl, either of which can be optionally substituted. When the bipyridyl or phenanthrolinyl is substituted, the substituents are preferably selected from among C1 to C4 alkyl groups, phenyl groups and phenyl groups substituted further with C1-C4 alkyl, especially C1-C2 alkyl groups. The substituted bipyridyl and phenatrolinyl liganding groups can be monosubstituted, disubstituted, or higher substituted. In various embodiments, disubstituted liganding groups can be used. Non-limiting examples include 4,4'-disubstituted-2,2'-bipyridyl, 5,5'-disubstituted-2,2'-bipyridyl, 1,10-phenanthrolinyl, 4,7-disubstituted-1,10-phenanthrolinyl and 5,6-disubstituted-1,10-phenanthrolinyl.

When only one of R and R' is a bipyridyl or phenanthrolinyl or one of the optionally substituted groups discussed above, the other is preferably selected from aliphatic ligands containing two nitrogen atoms capable of forming coordinate bonds with the metal M. Non-limiting examples include 1,3-propanediamine, 1,4-butanediamine and derivatives of either, where the derivatives are based on 1,3-propanediamine or 1,4-butanediamine skeletons optionally substituted with alkyl, aryl, or other groups that do not interfere with coordinate bonding of the nitrogens to the metal M or with the electrochemical activity of the complex.

In preferred embodiments, the transition metal compounds have one or more of the following characteristics: a suitable redox potential to operate as an electron shuttle in the biosensors of the invention, the potential generally being intermediate between that of the prosthetic group of the biomolecule and the biosensor electrode potential; the ability to exchange electrons rapidly with electrodes, the ability to rapidly transfer electrons to or rapidly accept electrons from an enzyme to accelerate the kinetics of electrooxidation or electroreduction of a substrate in the presence of an enzyme or another electrochemically active redox complex catalyst.

In a preferred embodiment, the transition metal compound comprises a cation with a formal +3 charge having the structure:

The invention also provides for methods of preparing transition metal compounds that can function as redox mediators having a structure that corresponds to formula I described above. In a preferred embodiment of the method, the transition metal compound is formed by ligand exchange of a precursor compound of general formula II above with a linking ligand. The transition metal compounds described herein comprise filler ligands Z that help form a stable complex with the metal and are displaceable by the linking ligand under the conditions of the ligand exchange. Preferred linking ligands comprise a nitrogenous moiety that provides a metal-to-nitrogen coordinate bond to the metal. In a preferred embodiment, the metal is osmium, Z is chlorine and the linking ligand is 3-aminopropylimidazole.

In another embodiment, the transition metal compounds are used as redox mediators as part of an electrochemical tag. The electrochemical tag is obtained when the transition metal compound is attached to a redox biomolecule via the linking ligand. In various embodiments, the transition metal compound is covalently attached to amino acids of the redox biomolecule to form the electrochemical tag. Preferably, the transition metal compound is attached to the amino acid residues of the redox biomolecule that are in relative proximity to the active-site prosthetic groups of the redox biomolecule. In a preferred embodiment, the transition metal compound is attached to glucose oxidase at aspartate and glutamate residues. Computer graphic analysis shows that at least two glutamate and eight aspartate residues are within at least 16 Angstroms from the flavin adenine dinucleotide (FAD) N5 atom of the FAD/FADH prosthetic groups within the 160 kiloDalton glucose oxidase homodimer.

In a preferred embodiment, the present invention provides for an electrochemical tag comprising a redox mediator that is a transition metal compound of general formula I and a redox biomolecule, for example an oxidoreductase. In a particularly preferred embodiment, the metal of the transition metal compound is osmium and the linking ligand is 3-aminopropylimidazole. In a preferred embodiment, the electrochemical tag comprises a redox mediator that is a transition metal compound of formula I covalently attached to glucose oxidase.

In further embodiments, the present invention provides methods of covalently attaching the transition metal compound to a redox biomolecule to form the electrochemical tag. In a preferred embodiment, the transition metal compound is attached to the redox biomolecule by carbodiimide coupling using, for example, 1-ethyl-3-(3-(dimethylamino)propyl)carbodiimide hydrochloride (EDC) and N-hydroxysulfosuccinimide (NHS), which are known to those skilled in the art. Without being bound by theory, carbodiimide catalyzes the formation of amide bonds between carboxylic acids or phosphates and amines by activating carboxyl or phosphate to form an O-urea derivative. This derivative can react readily with nucleophiles. The reagent can be used to make ether links from alcohol groups and ester links from acid and alcohols or phenols and peptide bonds from acid and amines. Carbodiimide is often used in the synthesis of peptides as the water-soluble derivative EDC or as the organic soluble derivative, N,N'-dicyclohexyl-carbodiimide (DCC). NHS is often used to assist the carbodiimide coupling in the presence of EDC. The reaction can include formation of the intermediate active ester (the product of condensation of the carboxylic group and N-hydroxysuccinimide) that further reacts with the amine function to yield finally the amide bond.

The invention also provides, in various embodiments, methods for using the electrochemical tag to electrochemically determine an analyte in a sample. Without limiting the mechanism, function or utility of present invention, it is believed that such methods take advantage of the efficient electron transfer from the electrochemical tag to the electrodes of the biosensors of the invention. The methods of the present invention can be applied to the determination of a wide variety of analytes in a wide range of samples.

In a non-limiting example, an electrochemically active redox complex comprising the electrochemical tag is formed at the surface of a solid support, such as an electrode and electron transfer is detected. In one embodiment, the complex is formed at the surface by virtue of attraction to or binding of analyte with a probe that either is immobilized on the electrode surface or is able to bind to the electrode surface. The binding of analyte to probe depends on the analyte (the "target") to be detected. For example, where the analyte is nucleic acid, a suitable probe is a nucleic acid comprising a single-stranded region complementary to a specific sequence of the analyte. The analyte to be determined can comprise nucleic acid, which may be single stranded or double stranded, as specified, or contain portions of both double stranded or single stranded sequence. Where the analyte comprises only double stranded nucleic acid, it is understood that strand separation is required prior to hybridization of the analyte to the complementary probe. The analyte may be DNA (either genomic or cDNA), RNA, or a hybrid, where the nucleic acid contains any combination of deoxyribo- and ribo-nucleotides and any combination of bases, including uracil, adenine, thymine, cytosine, guanine, inosine, xathanine and hypoxathanine, etc. Where the analyte to be detected comprises an antigen, a suitable probe is an antibody that specifically recognizes the antigen. Alternatively, where the target analyte is an antibody, the probe can comprise an antigen recognized by the antibody. The binding of analyte to probe can be, in a non-limiting example, by hybridization, annealing, charge-charge interaction, hydrophobic interaction, or covalent bonding. Generally, the probes can comprise, for example, oligonucleotides, including DNA, mRNA, rRNA, tRNA, peptide nucleic acids (PNAs), expressed sequence tags (ESTs), antigen, antibody, ligand or receptor.

The interaction between the electrochemical tag and the analyte is achieved utilizing a variety of recognition pairs that are known to those skilled in the art. In a non-limiting example, a recognition pair consists of biotin and avidin. To use the recognition pair, the respective members of the pair are covalently attached to the analyte and the electrochemical tag. Specific interaction of the two members of the pair causes a complex to be formed that contains the two chemical species and the covalently bound recognition pairs.

Thus, in one embodiment, the complex is formed at the electrode surface by interaction of immobilized probe on the electrode surface, analyte labeled with a first member of a recognition pair and electrochemical tag labeled with a second member of the recognition pair. The labeled components are combined in solution with an oxidation substrate of the redox biomolecule and the solution placed in contact with the electrode. The electrode is operated at a suitable potential to efficiently accept the electrons from the oxidation substrate by way of the metal compound covalently attached to the redox biomolecule as described above. The probe and analyte specifically bind or hybridize to each other, as discussed above. Since the probe is immobilized onto the surface of the electrode, hybridization of the analyte onto the probe results in bringing the electrochemical tag into proximity to the electrode, where electron transfer can occur.

In preferred embodiments, the methods are used in genetic diagnosis. For example, oligonucleotide probes can be used for determining target analyte sequences such as the gene for p53, which is a gene associated with a variety of cancers. Other non-limiting examples include the gene for nonpolyposis colon cancer, the BRCA1 breast cancer gene, the Apo E4 gene that indicates a greater risk of Alzheimer's disease allowing for easy presymptomatic screening of patients, mutations in the cystic fibrosis gene, or any of the others well known in the art.

In one preferred embodiment, direct amperometric detection of target p53 gene is performed using mRNA extracted from rat liver using an electrochemical tag comprising an avidin conjugated-glucose oxidase covalently attached to the transition metal compound. Utilizing techniques known in the art, the mRNA is optionally further prepared by converting the mRNA into cDNA, which is then labeled with biotin. An electrochemically active redox complex is formed at the electrode surface where probe is bound to the electrode, analyte is bound to probe via nucleic acid hybridization and electrochemical tag is bound to analyte via recognition pair binding involving avidin and biotin, respectively. As explained elsewhere, those skilled in the art will recognize that one is not limited to the use of biotin/avidin recognition pairs and that a variety of recognition pairs exist that can be utilized in accordance with the present invention. Thus the electrochemical tag is brought to the electrode surface following target analyte hybridization. In the presence of substrate (in this case glucose), the electrochemical tag comprising the redox biomolecule (in this case glucose oxidase) catalyzes the oxidation of substrate and the electrons are shuttled to the electrode surface by the transition metal compound attached to the redox biomolecule backbone. The determination or detection of analyte is determined by detection of electron transfer between the electrochemically active redox complex and the electrode. A current is detected when the shuttled electrons are picked up by the electrode.

In a further embodiment, the analyte to be detected is also the oxidation substrate for the redox biomolecule. In a non-limiting example, the redox biomolecule component of the electrochemical tag comprises glucose oxidase and the analyte is glucose. The presence of the oxidation substrate is detected as electron transfer activity at the electrode (detection of current or voltage), where the electrochemical tag is held or formed at the electrode surface utilizing techniques known in the art. In a non-limiting example, the surface of the electrode is labeled with a first member of a recognition pair and the electrochemical tag is labeled with a second member. The labeled components can be combined in solution with the sample containing the analyte to be detected (in this case, for example, glucose), which is also the oxidation substrate of the redox biomolecule. Binding of the members of the recognition pair to each other results in bringing the electrochemical tag into proximity to the electrode, where electron transfer can occur. The electrochemical tag comprising glucose oxidase catalyzes the oxidation of any glucose present in the sample and the electrons are shuttled to the electrode surface by the transition metal compound attached to the glucose oxidase backbone. The determination or detection of glucose is determined by detection of electron transfer between the electrochemical tag and the electrode. A current is detected when the shuttled electrons are picked up by the electrode.

In a preferred embodiment, probe is attached to gold electrodes. However, one skilled in the art knows that the probe can be immobilized to the electrode by a number of techniques known in the art. For example, recognition pairs can be used to attach probe to electrode. In this regard, the probe can be modified to comprise a first member of a recognition pair where the electrode surface is coated with a second member, the recognition pair being distinct from the recognition pair used for binding of analyte to the electrochemical tag. In further examples, the probes of the present invention can be covalently attached to thin film oxidized surfaces. Employing literature procedures, a variety of techniques are available and known to those skilled in the art for immobilizing probes onto the surface of electrodes for use in accordance with the present invention.

In various other embodiments, viral and bacterial detection can be carried out using the complexes of the invention. In this embodiment, probes are designed to detect target sequences from a variety of bacteria and viruses. The methods disclosed herein allow for direct screening of clinical samples to detect, for example, HIV nucleic acid sequences. In addition, this allows direct monitoring of circulating virus within a patient as an improved method of assessing the efficacy of anti-viral therapies. Similarly, viruses associated with leukemia, HTLV-1 and HTLV-II, may be detected in this way. Bacterial infections such as tuberculosis may also be detected.

In other embodiments, nucleic acids are used as probes for toxic bacteria in the screening of, for example water and food samples. For example, samples may be treated to lyse the bacteria to release its nucleic acid and then probes designed to recognize bacterial strains, including, but not limited to, such pathogenic strains as, *Salmonella, Campylobacter, Vibrio cholerae*, enterotoxic strains of *E. coli* and Legionnaire's disease bacteria. Similarly, bioremediation strategies may be evaluated using the compositions of the invention.

In other embodiments, the probes can be used for forensics where DNA fingerprinting is used to match crime-scene analytes such as DNA against samples taken from victims and suspects.

The source of analyte can include, for example, humans, animals, plants, or environment.

In other embodiments, the present invention is also directed to kits comprising electrochemical tags. The kits can further comprise probes, such as those described herein, which can recognize and bind to the analyte to be detected.

In various other embodiments, the present invention is further directed to a biosensor that utilizes the electrochemical tags described herein. The biosensor may comprise an apparatus or be used in a system that includes the necessary components for detecting and measuring a signal produced by one or more electrochemical tags. An apparatus can comprise integrated circuits including a biosensor array combined with a power supply and a detector. Such integrated circuits are known to those of skill in the art. Systems including the biosensor array may additionally include means for measuring an electrochemical signal after a potential is applied across a working electrode. Applying the electrical potential and measuring the electrochemical signal can be accomplished with a programmed processor. The signal to be detected can be, for example, measured by pulse amperometry, by intermittent pulse amperometry, or differential pulse amperometry. Alternatively, the biosensor may comprise a single working electrode and a single reference electrode. Whether in an array or a single working electrode, the biosensor may optionally include one or more counter electrodes.

The methods and apparatus described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

The headings (such as "Background of the Invention" and "Summary of the Invention") used herein are intended only for general organization of topics within the disclosure of the invention and are not intended to limit the disclosure of the invention or any aspect thereof. In particular, subject matter disclosed in the "Background of the Invention" may include aspects of technology within the scope of the invention and may not constitute a recitation of prior art. Subject matter disclosed in the "Summary of the Invention" is not an exhaustive or complete disclosure of the entire scope of the invention or any embodiments thereof.

The citation of references herein does not constitute an admission that those references are prior art or have any relevance to the patentability of the invention disclosed herein. All references cited in the specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

As used herein, the word "include," and its variants, is intended to be non-limiting, such that recitation of items in a list is not to the exclusion of other like items that may also be useful in the materials, compositions, devices and methods of this invention.

In the following description the terms "determination" or "detection" will be used to denote both qualitative and quantitative determination or detection of analyte. Where, for example, the method and system defined below are used for determining or detecting an analyte in a liquid medium, this is meant to denote determining the presence of an analyte in the medium and optionally its concentration.

The term "analyte" as used herein and will be used further below, is meant to denote an agent determined in a liquid sample. Analyte may or may not be the substrate for a redox biomolecule.

The term "redox biomolecule" as used herein and will be used further below, is meant to denote biomolecules, native or otherwise modified or engineered, that are inherently capable of electron transfer, such as for example, enzymes that catalyze the oxidation or reduction of a substrate or a group of substrates. Some redox biomolecules use prosthetic groups, such as flavins or nicotinamide adenine dinucleotide (NAD). A prosthetic group is the non-protein component of the redox biomolecule that is bound to the redox biomolecule enabling it to catalyze oxidation or reduction. The simplest redox biomolecules, in which no prosthetic group is present, are those that use reversible formation of a disulfide bond between two cysteine residues, as in thioredoxin. Many use the ability of iron or copper ions to exist in two different redox states.

The term "substrate" or "oxidation substrate" as used herein and will be used further below, is meant to denote a molecule that binds to a redox biomolecule active site and undergoes a reaction, such as oxidation or reduction.

The term "redox mediator" as used herein and will be used further below, is meant to denote molecules that are used to carry electrons between the redox biomolecule and the electrode.

The term "electrochemical tag" as used herein and will be used further below, is meant to denote a redox biomolecule covalently attached to a redox mediator.

The term "electrochemically active redox complex" as used herein and will be used further below, is meant to denote a complex formed at the surface of an electrode comprising the electrochemical tag.

The term "biosensor" as used herein and will be used further below, is meant to denote an apparatus or system that comprises the necessary components for detecting or measuring a signal produced by movement of electrons produced in an oxidation and reduction reaction (for example, amperometric detection). The term "biosensor" includes devices for determining the concentration of substances and other parameters of biological interest even where a biological system is not directly utilized.

EXAMPLES

The following examples are intended to be illustrative and are not intended to limit the scope of the invention.

Example 1

This example illustrates the synthesis of the redox mediator, $Os(bpy)_2$(3-aminopropylimidazole)Cl.

$Os(bpy)_2Cl_2$ is synthesized from $K_2OsCl_6$ (99%, Stem Chemicals) following the proposed procedure as described, for example, in Lay, P. A. et al., 1986, Inorg. Synth., 24: 291-296. $Os(bpy)_2$(3-aminopropylimidazole)Cl is synthesized as follows: To a solution of $Os(bpy)_2Cl_2$ (0.10 mmol) in 6.0 ml fresh-distilled ethylene glycol is added 3-aminopropylimidazole (0.12 mmol) in one portions the result mixture is refluxed for 90-120 min. 3-aminopropylimidazole was purchased from Sigma-Aldrich (St. Louis, Mo.). The completion of the ligand-exchange reaction is monitored by cyclic voltammetry. The purple reaction mixture is then poured slowly into 200 ml of rapid stirred ether. The precipitate is collected by suction filtration through a fine fritted funnel. The crude product is washed with ether, dissolved in 3.0-5.0 ml of ethanol and precipitated again from ether. The precipitate is further purified by crystallization from ethanol giving the pure product in 75% yield.

The product shows a single pair of reversible redox waves at a gold electrode with an $E_{1/2}$ of 0.19 V in phosphate buffered saline (PBS). To ensure a complete ligand-exchange, slight excess of 3-aminopropylimidazole (10-20%) is required.

Cyclic voltammetry is used to monitor the course of the reaction. The purified product is characterized by mass spectrometry and electrochemistry, which are consistent with the structure of:

Example 2

This example illustrates the modification of the redox biomolecule, glucose oxidase (GOx), by coupling to a redox mediator.

Glucose oxidase-avidin D conjugate (GOx-A) (131 units/mg of solid) was purchased from Vector Laboratories (San Diego, Calif.). Glucose oxidase (GOx, EC 1.1.3.4, type X-S, from *Aspergillus niger*, 213 units/mg of solid) was purchased from Sigma-Aldrich (St. Louis, Mo.). 1-ethyl-3-(3-(dimethylamino)propyl)carbodiimide hydrochloride (EDC), N-hydroxysulfosuccinimide (Sulfo-NHS) and dialysis kits (MWCO 10,000) were obtained from Pierce.

GOx is covalently modified with $Os(bpy)_2$(3-aminopropylimidazole)Cl by amide bond formation between GOx carboxylates and the aliphatic primary amino groups present on the redox mediators (e.g. transition metal compound) with EDC/NHS as coupling agent. Excess redox mediator is used to avoid protein self-crosslinking.

To 4.5 ml of 1.0 mM $Os(bpy)_2$(3-aminopropylimidazole)Cl and 1.0 µM avidin-conjugated glucose oxidase (GOx-A) in DI water, is added 1-ethyl-3-(3-dimethylaminopropyl)-carbodiimide (EDC) and N-hydroxysuccinimide (NHS), yielding final concentrations of 4.0 mM EDC and 1.6 mM sulfo-NHS. The mixture is stirred for 2 h at room temperature. The solution is then purified by dialysis against PBS buffer for 24 h. In a control experiment, same amount of GOx-A is mixed with Os complex without adding coupling agent.

Example 3

This example illustrates that the electrochemical tag of GOx modified by covalent attachment of the transition metal compound $Os(bpy)_2$(3-aminopropylimidazole)Cl is electrochemically active.

Figure 1:
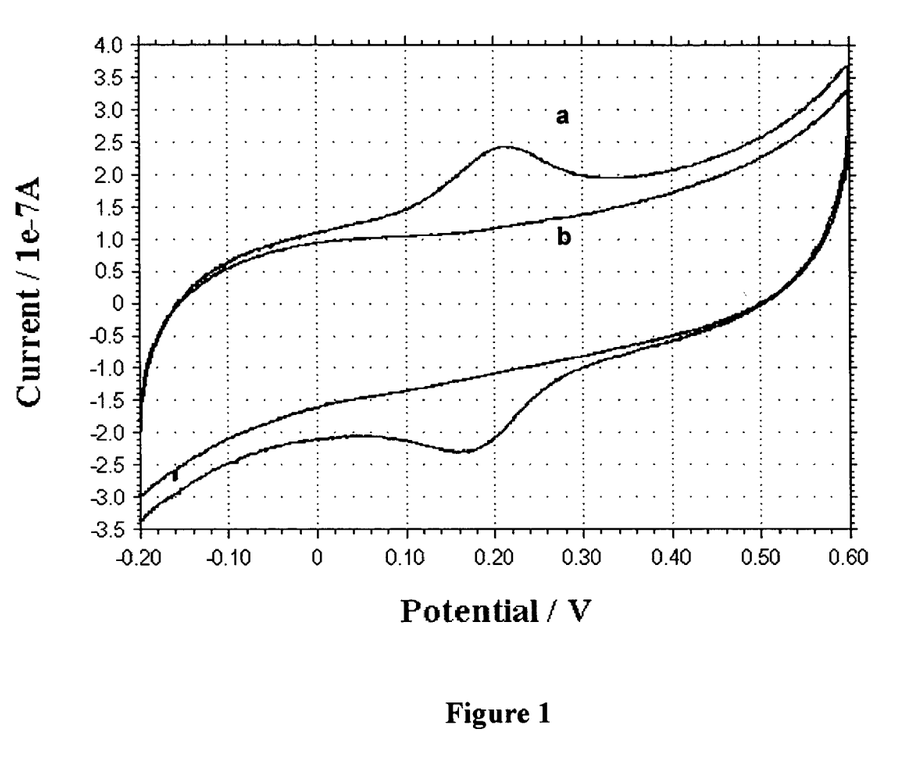
FIG. 1 is an illustration of data describing cyclic voltammetry of Os(bpy)$_2$(3-aminopropylimidazole)Cl modified glucose oxidase (GOx) adsorbed on screen-printed carbon electrode in PBS buffer. (a) in the presence of EDC/NHS coupling agent, (b) in the absence of EDC/NHS coupling agent. Scan rate: 100 mV/s.

Electrochemical experiments are carried out using a CH Instruments model 660A electrochemical workstation coupled with a low current module (CH Instruments, Austin, Tex.). The three-electrode system consists of a 2-mm-diameter gold working electrode, a miniature Ag/AgCl reference electrode (Cypress Systems, Lawrence, Kans.) and a platinum wire counter electrode. Potentials are referred to the Ag/AgCl reference electrode. Cyclic voltammetry (CV) of the electrochemical tag shows a pair of well-defined voltammetric current peaks centered at 0.19 V, showing electrochemical activity. To prove that the enzyme was indeed covalently modified, as opposed to simple electrostatic association with $Os(bpy)_2$(3-aminopropylimidazole)Cl, a control experiment is performed according to example 2 but in the absence of the EDC and NHS coupling reagents. The control experiment yields biologically active enzyme but with no detectable mediator following dialysis, indicating that the mediator is not covalently attached to GOx (curve b in FIG. 1).

Example 4

This example illustrates characterization of GOx modified with $Os(bpy)_2$(3-aminopropylimidazole)Cl using UV-vis absorbance spectra.

Figure 2:
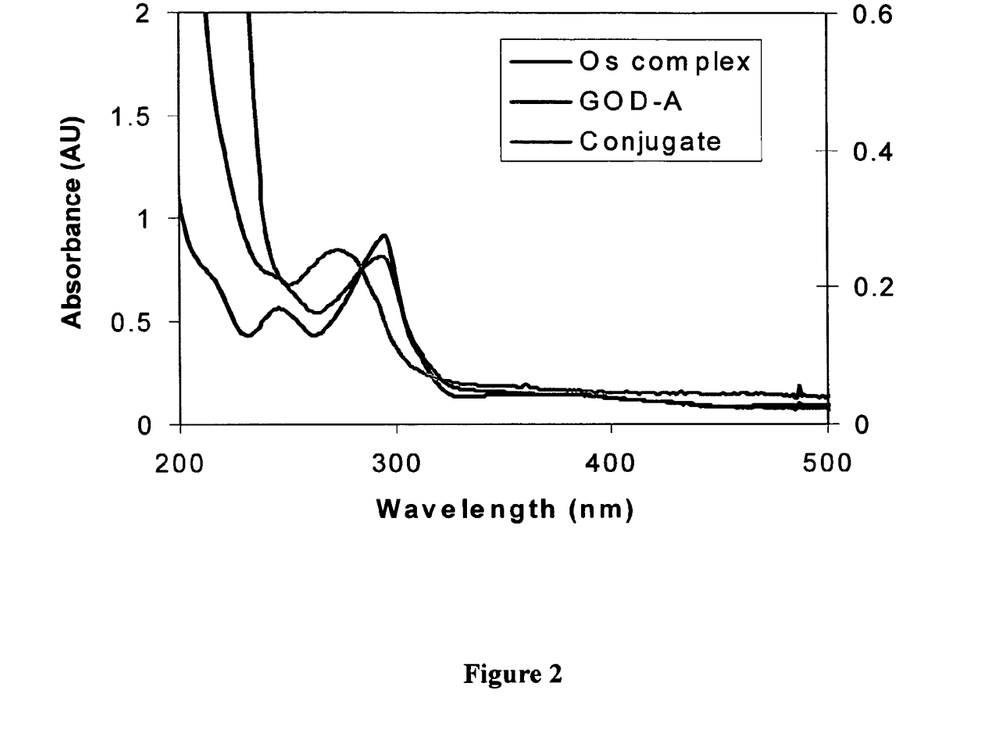
FIG. 2 is an illustration of UV-Vis spectra of (a) GOx (b) Os(bpy)$_2$(3-aminopropylimidazole)Cl and (c) Os(bpy)$_2$(3-aminopropylimidazole)Cl modified GOx.

UV-vis absorbance spectra of the starting materials and the modified GOx are depicted in FIG. 2. UV-vis spectrum $Os(bpy)_2$(3-aminopropylimidazole)Cl is similar to that of $Os(bpy)_2$ compound. It exhibits intense band in the UV region due to intraligand (IL)$\sigma \rightarrow \sigma^*$(bpy) transitions and by a broad band in the visible region (400-600 nm) due to spin allowed $Os(d\pi) \rightarrow bpy(\pi^*)$ metal-to-ligand charge-transfer (MLCT) transition. Moreover, the spectrum of the modified GOx is a composite of the absorbance spectra from both the GOx and $Os(bpy)_2Cl$(3-aminopropylimidazole) complex. A simple overlay of $Os(bpy)_2Cl$(3-aminopropylimidazole) and GOx generates a spectrum which is similar to that of the activated GOx, confirming the formation of the activated GOx.

Example 5

This example illustrates the biological activity of GOx modified with $Os(bpy)_2$(3-aminopropylimidazole)Cl using UV-vis absorbance spectra.

Figure 3:
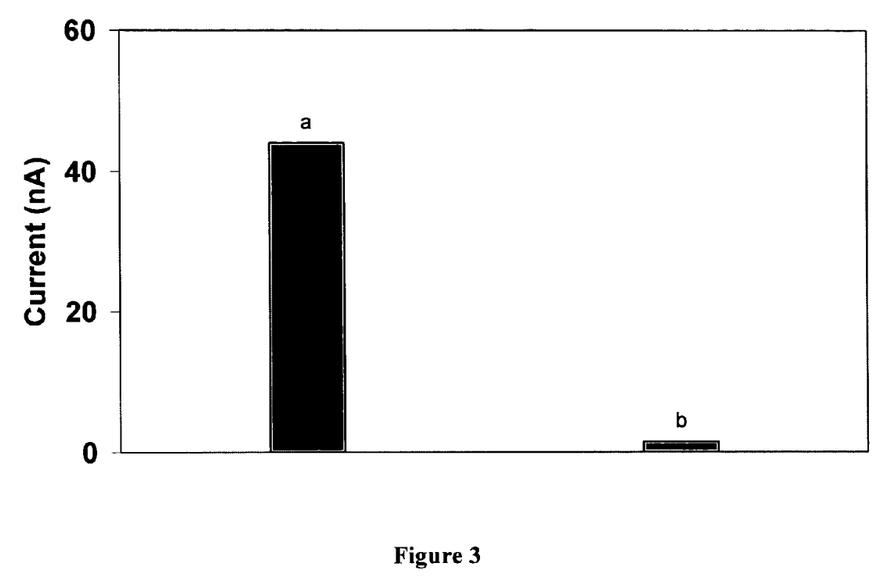
FIG. 3 is an illustration of amperometric response of Os(bpy)$_2$(3-aminopropylimidazole)Cl modified GOx adsorbed on a screen-printed carbon electrode. (a) in the presence of EDC/NHS coupling agent, (b) in the absence of EDC/NHS coupling agent. Poised potential: 0.30 V, glucose concentration: 40 mM.

To determine whether enzyme is still biologically active after the covalent modification, one drop of the modified enzyme solution is applied to a screen-printed carbon electrode. After 5-10 min adsorption, the electrode is thoroughly rinsed with PBS buffer. Catalytic current is monitored by measuring the current at 0.3 V in the presence of 40 mM glucose solution in PBS. Amperometric results of immobilized electroactive enzyme reveal that the GOx retains its catalytic activity toward the oxidation of glucose (FIG. 3). The catalytic current is comparable to or better than that of native GOx at same concentration in the presence of the best soluble mediator. Amperometric results further prove that the $Os(bpy)_2$(3-aminopropylimidazole)Cl covalently attached to the GOx could promote direct reduction of the FAD centers of the enzyme without the need of any additional mediator in solution. Similarly, GOx-Avidin conjugates modified with $Os(bpy)_2$(3-aminopropylimidazole)Cl show similar electrochemical properties as those of the activated GOx.

Example 6

This example illustrates the application of GOx-A modified with $Os(bpy)_2$(3-aminopropylimidazole)Cl as an electrochemical tag in nucleic acid detection.

Figure 4:
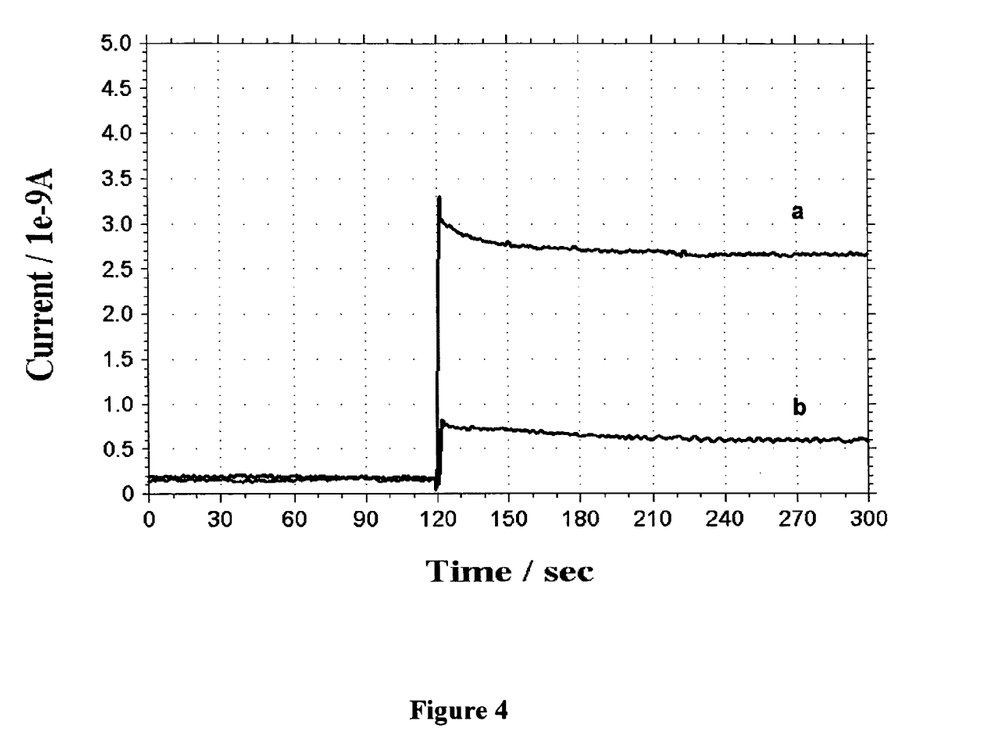
FIG. 4 is an illustration of amperometric response of DNA assay (p53 gene in mRNA, 20 pg/µl) using Os(bpy)$_2$(3-aminopropylimidazole)Cl modified enzyme as electrochemical tag. (a) with capture probe complementary to p53 gene (b) with capture probe non-complementary to p53 gene. Conditions are the same as described in FIG. 3.

The electrochemically activated GOx-A is used as an electrochemical tag in direct amperometric detection of nucleic acid. FIG. 4 shows a typical amperometric curve for the detection of p53 gene in mRNA (20 pg/μl) extracted from rat liver (mRNA is converted to cDNA, which is then labeled with biotin). Nucleic acid preparation, capture probe immobilization and measurements were essentially as described, for example, in Xie, H. et al., 2004, Nucleic Acids Research, 32: e15. When complementary probe is immobilized on the electrode surface, the enzyme is brought to the surface following target gene hybridization because the avidin moiety of GOx-A binds to the biotin moiety of the target. In the presence of glucose, the enzyme catalyzes the oxidation of glucose. The electrons are then being shuttled to the electrode surface by Os(bpy)$_2$(3-aminopropylimidazole)Cl attached to the GOx-A backbone and picked up by the electrode. In a control experiment with non-complementary capture probe on the electrode surface, the target p53 gene fails to hybridize to the capture probe and hence enzyme is unable to bind onto the surface. The small current being detected is mainly due to non-specific binding of enzyme. Table 1 gives the results of three duplicated experiments.

TABLE 1

Amperometric response of p53 assay (3 replicates)

|  | 1 | 2 | 3 |
|---|---|---|---|
| Sample | 2.53 nA | 2.50 nA | 2.34 nA |
| Control | 0.60 nA | 0.46 nA | 0.43 nA |

As various changes could be made in the above methods and compositions without departing from the scope of the present teachings, it is intended that all matter contained in the above description be interpreted as illustrative and not in a limiting sense. Illustrations and examples are not intended to be a representation that given embodiments of this present teachings have, or have not, been performed.

What is claimed is:

1. A transition metal compound of the formula:

wherein
   M is a metallic element that can form a coordinate bond to nitrogen;
   R and R' are nitrogen-containing organic moieties coordinated to M at their nitrogen atoms, wherein R and R' are independently selected from the group consisting of 2,2-bipyridyl and 2,2'-bipyridyl substituted with one or more substituents selected from the group consisting of $C_1$-$C_4$ alkyl, phenyl and phenyl substituted with one or more $C_1$-$C_4$ alkyl groups;
   n is an integer of 1 to 20, inclusive;
   Z is a halogen atom;
   m is +1, +2, +3, +4, +5, or +6; and
   X is an anion, or combination of anions, that balances m.

2. A compound as set forth in claim 1 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

3. A compound as set forth in claim 2 wherein M is osmium.

4. A compound as set forth in claim 1 wherein Z is chloro or bromo.

5. A compound as set forth in claim 1 wherein R and R' are independently selected from the group consisting of 2,2'-bipyridyl, 4,4'-methyl-2,2'-bipyridyl, 4,4'-ethyl-2,2'-bipyridyl, 4,4'-phenyl-2,2'-bipyridyl, 5,5'-methyl-2,2'-bipyridyl, 5,5'-ethyl-2,2'-bipyridyl and 5,5'-phenyl-2,2'-bipyridyl.

6. A compound as set forth in claim 5 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

7. A compound as set forth in claim 6 wherein M is osmium.

8. A compound as set forth in claim 5 wherein Z is chloro or bromo.

9. A compound as set forth in claim 1 having the formula:

10. A method for preparing a transition metal compound, the method comprising contacting a precursor compound of the formula:

wherein Z, M, R, R', X and m are as defined in claim 1, with a linking ligand to form the transition metal compound of claim 1.

11. A method as set forth in claim 10 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

12. A method as set forth in claim 11 wherein M is osmium.

13. A method as set forth in claim 10 wherein Z is chloro or bromo.

14. A method as set forth in claim 10 wherein R and R' are independently selected from the group consisting of 2,2'-bipyridyl, 4,4'-methyl-2,2'-bipyridyl, 4,4'-ethyl-2,2'-bipyridyl, 4,4'-phenyl-2,2'-bipyridyl, 5,5'-methyl-2,2'-bipyridyl, 5,5'-ethyl-2,2'-bipyridyl and 5,5'-phenyl-2,2'-bipyridyl.

15. A method as set forth in claim 14 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

16. A method as set forth in claim 15 wherein M is osmium.

17. A method as set forth in claim 14 wherein Z is chloro or bromo.

18. A method as set forth in claim 10 wherein at least one of R and R' is 2,2'-bipyridyl, M is osmium, Z is chlorine and the linking ligand is 3-aminopropylimidazole.

19. A method as set forth in claim 10, wherein the precursor compound is a compound of the formula:

wherein
R and R' are 2,2'-bipyridyl and are coordinated to Os at their nitrogen atoms,
Z is chloro,
m is +3,
X is an anion, or combination of anions, that balances m;
the linking ligand is 3-aminopropylimidazole; and
the transition metal compound is a compound of the formula:

20. An electrochemical tag comprising a redox biomolecule bonded to a transition metal compound of the formula:

wherein
M is a metallic element that can form a coordinate bond to nitrogen;
R and R' are nitrogen-containing organic moieties coordinated to M at their nitrogen atoms, wherein R and R' are independently selected from the group consisting of 2,2'-bipyridyl and 2,2'-bipyridyl substituted with one or more substituents selected from the group consisting of $C_1$-$C_4$ alkyl, phenyl and phenyl substituted with one or more $C_1$-$C_4$ alkyl groups;
n is an integer of 1 to 20, inclusive;
Z is a halogen atom;
m is +1, +2, +3, +4, +5, or +6; and
X is an anion, or combination of anions, that balances m.

21. An electrochemical tag as set forth in claim 20 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

22. An electrochemical tag as set forth in claim 21 wherein M is osmium.

23. An electrochemical tag as set forth in claim 20 wherein the redox biomolecule comprises an oxidoreductase.

24. An electrochemical tag as set forth in claim 23 wherein the oxidoreductase comprises glucose oxidase.

25. An electrochemical tag as set forth in claim 20 wherein Z is chloro or bromo.

26. An electrochemical tag as set forth in claim 20 wherein R and R' are independently selected from the group consisting of 2,2'-bipyridyl, 4,4'-methyl-2,2'-bipyridyl, 4,4'-ethyl-2,2'-bipyridyl, 4,4'-phenyl-2,2'-bipyridyl, 5,5'-methyl-2,2'-bipyridyl, 5,5'-ethyl-2,2'-bipyridyl and 5,5'-phenyl-2,2'-bipyridyl.

27. An electrochemical tag as set forth in claim 26 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

28. An electrochemical tag as set forth in claim 27 wherein M is osmium.

29. An electrochemical tag as set forth in claim 26 wherein the redox biomolecule comprises an oxidoreductase.

30. An electrochemical tag as set forth in claim 29 wherein the oxidoreductase comprises glucose oxidase.

31. An electrochemical tag as set forth in claim 26 wherein Z is chloro or bromo.

32. An electrochemical tag as set forth in claim 20 wherein at least one of R and R' is 2,2'-bipyridyl, M is osmium, Z is chloro and n is 3.

33. An electrochemical tag as set forth in claim 32 wherein the redox biomolecule comprises an oxidoreductase.

34. An electrochemical tag as set forth in claim 33 wherein the oxidoreductase comprises glucose oxidase.

35. An electrochemical tag as set forth in claim 20 comprising a redox biomolecule bonded to a transition metal compound of the formula:

36. An electrochemical tag as set forth in claim 35 wherein the redox biomolecule comprises an oxidoreductase.

37. An electrochemical tag as set forth in claim 36 wherein the oxidoreductase comprises glucose oxidase.

38. A method for preparing an electrochemical tag as set forth in claim 20, the method comprising bonding a redox biomolecule to a transition metal compound of the formula:

wherein
M is a metallic element that can form a coordinate bond to nitrogen;
R and R' are nitrogen-containing organic moieties coordinated to M at their nitrogen atoms, wherein R and R' are independently selected from the group consisting of 2,2'-bipyridyl and 2,2'-bipyridyl substituted with one or more substituents selected from the group consisting of $C_1$-$C_4$ alkyl, phenyl and phenyl substituted with one or more $C_1$-$C_4$ alkyl groups;
n is an integer of 1 to 20, inclusive;
Z is a halogen atom;
m is +1, +2, +3, +4, +5, or +6; and
X is an anion, or combination of anions, that balances m.

39. A method as set forth in claim 38 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

40. A method as set forth in claim 39 wherein M is osmium.

41. A method as set forth in claim 38 wherein the redox biomolecule comprises an oxidoreductase.

42. A method as set forth in claim 41 wherein the oxidoreductase comprises glucose oxidase.

43. A method as set forth in claim 38 wherein the redox biomolecule is bound to the transition metal compound by an amide bond.

44. A method as set forth in claim 38 wherein Z is chloro or bromo.

45. A method as set forth in claim 38 wherein R and R' are independently selected from the group consisting of 2,2'-bipyridyl, 4,4'-methyl-2,2'-bipyridyl, 4,4'-ethyl-2,2'-bipyridyl, 4,4'-phenyl-2,2'-bipyridyl, 5,5'-methyl-2,2'-bipyridyl, 5,5'-ethyl-2,2'-bipyridyl and 5,5'-phenyl-2,2'-bipyridyl.

46. A method as set forth in claim 45 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

47. A method as set forth in claim 46 wherein M is osmium.

48. A method as set forth in claim 45 wherein the redox biomolecule comprises an oxidoreductase.

49. A method as set forth in claim 48 wherein the oxidoreductase comprises glucose oxidase.

50. A method as set forth in claim 45 wherein the redox biomolecule is bound to the transition metal compound by an amide bond.

51. A method as set forth in claim 45 wherein Z is chloro or bromo.

52. A method as set forth in claim 38 wherein at least one of R and R' is 2,2'-bipyridyl, M is osmium, Z is chloro and n is 3.

53. A method as set forth in claim 52 wherein the redox biomolecule comprises an oxidoreductase.

54. A method as set forth in claim 53 wherein the oxidoreductase comprises glucose oxidase.

55. A method as set forth in claim 52 wherein the redox biomolecule is bound to the transition metal compound by an amide bond.

56. A method as set forth in claim 38, wherein the method comprises binding a redox biomolecule to a transition metal compound of the formula:

57. A method as set forth in claim 56 wherein the redox biomolecule comprises an oxidoreductase.

58. A method as set forth in claim 57 wherein the oxidoreductase comprises glucose oxidase.

59. A method as set forth in claim 57 wherein the redox biomolecule is bound to the transition metal compound by an amide bond.

60. An electrochemical method for detecting an analyte in a sample, the method comprising:
   forming at an electrode surface an electrochemically active redox complex comprising the analyte and an electrochemical tag; and
   detecting electron transfer at the electrode, wherein the electrochemical tag comprises a redox biomolecule bonded to a transition metal compound of the formula:

wherein
M is a metallic element that can form a coordinate bond to nitrogen;
R and R' are nitrogen-containing organic moieties coordinated to M at their nitrogen atoms, wherein R and R' are independently selected from the group consisting of 2,2-bipyridyl and 2,2'-bipyridyl substituted with one or more substituents selected from the group consisting of $C_1$-$C_4$ alkyl, phenyl and phenyl substituted with one or more $C_1$-$C_4$ alkyl groups;
n is an integer of 1 to 20, inclusive;
Z is a halogen atom;
m is +1, +2, +3, +4, +5, or +6; and
X is an anion, or combination of anions, that balances m.

61. A method as set forth in claim 60 wherein M is selected from the group consisting of osmium, ruthenium, zinc, iron, rhodium, rhenium, platinum, scandium, titanium, vanadium, cadmium, magnesium, copper, cobalt, palladium, chromium, manganese, nickel, molybdenum, tungsten and iridium or mixtures thereof.

62. A method as set forth in claim 61 wherein M is osmium.

63. A method as set forth in claim 60 wherein the analyte is an oxidation substrate for the redox biomolecule.

64. A method as set forth in claim 60 wherein the redox biomolecule comprises an oxidoreductase.

65. A method as set forth in claim 64 wherein the oxidoreductase comprises glucose oxidase.

66. A method as set forth in claim 60 wherein Z is chloro or bromo.

67. A method as set forth in claim 60, wherein the method further comprises:
   immobilizing a probe onto the electrode surface;
   labeling the analyte with a first member of a recognition pair;
   labeling the electrochemical tag with a second member of the recognition pair; and
   combining the labeled components with an oxidation substrate of the redox biomolecule in solution in contact with the electrode, wherein the probe and analyte specifically bind or hybridize to each other.

68. A method as set forth in claim 67, wherein the recognition pair comprises biotin and avidin.

69. A method as set forth in claim 67, wherein the analyte comprises a nucleic acid.

70. A method as set forth in claim 60, wherein the method further comprises:
   labeling the electrode surface with a first member of a recognition pair;
   labeling the electrochemical tag with a second member of the recognition pair; and
   combining the labeled components with an oxidation substrate of the redox biomolecule in solution in contact with the electrode, wherein the electrochemical tag binds to the electrode surface.

71. A method as set forth in claim 70, wherein the recognition pair comprises biotin and avidin.

72. A method as set forth in claim 70, wherein the analyte comprises the substrate of the redox biomolecule.

73. A method as set forth in claim 60, wherein the transition metal compound comprises a +3 cation having the structure 74. A method as set forth in claim 73 wherein the redox biomolecule comprises an oxidoreductase.

75. A method as set forth in claim 73 wherein the oxidoreductase comprises glucose oxidase.

* * * * *